(12) United States Patent
Buckman et al.

(10) Patent No.: US 7,235,090 B2
(45) Date of Patent: Jun. 26, 2007

(54) METHOD AND APPARATUS FOR SOLID ORGAN TISSUE APPROXIMATION

(75) Inventors: Robert F. Buckman, Radnor, PA (US); Jay A. Lenker, Laguna Beach, CA (US); Donald J. Kolehmainen, Laguna Niguel, CA (US)

(73) Assignee: Damage Control Surgical Technologies, Inc.

( * ) Notice: Subject to any disclaimer, the term of this patent is extended or adjusted under 35 U.S.C. 154(b) by 708 days.

(21) Appl. No.: 10/358,735

(22) Filed: Feb. 4, 2003

(65) Prior Publication Data

US 2003/0176890 A1   Sep. 18, 2003

Related U.S. Application Data

(60) Provisional application No. 60/354,428, filed on Feb. 4, 2002.

(51) Int. Cl.
*A61B 17/08* (2006.01)
(52) U.S. Cl. .................. 606/215; 606/213; 606/218
(58) Field of Classification Search ............... None
See application file for complete search history.

(56) References Cited

U.S. PATENT DOCUMENTS

| | | | | |
|---|---|---|---|---|
| 2,485,531 A | * | 10/1949 | Dzus et al. ............... | 606/73 |
| 3,926,193 A | * | 12/1975 | Hasson ..................... | 606/218 |
| 4,402,445 A | * | 9/1983 | Green ...................... | 227/19 |
| 4,534,350 A | * | 8/1985 | Golden et al. ............. | 606/220 |
| 4,796,612 A | * | 1/1989 | Reese ....................... | 606/72 |
| 4,889,119 A | * | 12/1989 | Jamiolkowski et al. ..... | 606/220 |
| 5,268,000 A | * | 12/1993 | Ottieri et al. ............. | 606/62 |
| 5,486,196 A | | 1/1996 | Hirshowitz et al. ........ | 606/218 |
| 5,549,619 A | * | 8/1996 | Peters et al. ............... | 606/151 |
| 5,759,193 A | | 6/1998 | Burbank et al. ............ | 606/213 |
| 5,800,436 A | * | 9/1998 | Lerch ........................ | 606/72 |
| 5,910,144 A | * | 6/1999 | Hayashi .................... | 606/108 |
| 5,928,267 A | * | 7/1999 | Bonutti et al. ............. | 606/216 |

* cited by examiner

*Primary Examiner*—Anhtuan T. Nguyen
*Assistant Examiner*—Darwin P Erezo (57) ABSTRACT

Devices and methods are disclosed for achieving hemostasis in solid visceral wounds. Such devices and methods are especially useful in the emergency, trauma surgery or military setting. In such cases, the patient may have received trauma to the abdominal viscera. The devices utilize flexible, variable depth transfixing bolts that penetrate the viscera. These bolts are pulled tight to bring the tissue into apposition and hold said tissue in apposition while the wound heals. These bolts overcome the limitations of sutures that are currently used for the same purposes. The bolts come in a variety of lengths and diameters. Since the bolts are flexible, the curvature may be adjusted by the surgeon. The devices are flexible, bendable, and conformable in their wet or dry state. They can be used either straight or through a broad range of curvatures to suit the needs of various pathologies. The bolts include pressure plates that are capable of exerting compressive pressure over broad areas of visceral wounds without causing tearing of the friable parenchyma. The bolts may be placed and removed by open surgery or laparoscopic access.

20 Claims, 6 Drawing Sheets

METHOD AND APPARATUS FOR SOLID ORGAN TISSUE APPROXIMATION

The present application claims priority benefit under 35 USC § 119(e) from U.S. Provisional Application No. 60/354,428 filed Feb. 4, 2002, entitled "TRANSFIXING PARENCHYMAL BOLT SYSTEM" which is herein incorporated by reference.

FIELD OF THE INVENTION

The field of this invention relates to devices and methods for trauma and general surgery, combat medicine, and emergency medical services.

BACKGROUND OF THE INVENTION

As recently as the early 1990s, surgical operations for trauma were directed at the anatomic repair of all injuries at time of the initial operation. It was observed during these exercises that many patients became hypothermic, acidotic, and coagulopathic. Patients showing these three signs often died. Death often occurred in the operating room due to exsanguination, or postoperatively, due to the complications of prolonged shock and massive transfusion to replace blood lost as a result of the trauma.

One of the most notable developments in the recent evolution of surgery has been the reintroduction of the concept of staged laparotomy to overcome the deficiencies of the repair all-at-once approach. This new strategy of staged laparotomy employing new tactics that have been termed damage control is now used in 10% to 20% of all trauma laparotomies.

Sources of hemorrhage within the abdomen that are most difficult to manage include major stellate fractures in the thick, solid, parenchymal organs, especially the liver. Such injuries may involve more than one hepatic lobe, involve massive hemorrhage, and may be caused by severe blunt or penetrating trauma. While the control of most liver hemorrhage is simple, very severe anatomic wounds are difficult to manage and have a high mortality, sometimes exceeding 80%. Standard approaches to control of these wounds involve packing with gauze or omentum, if available, and deep liver sutures. Each of these techniques has serious limitations and often fails. A major technical problem has to do with the depth to which the sutures can be placed within the liver. The limitation of liver sutures to coapt or tamponade deep parenchymal wounds is clear for several reasons. Sutures may be attached to or come pre-mounted to needles of limited size and curvature making deep placement difficult or impossible. The sutures tend to tear through the friable parenchyma (the liver is especially subject to tearing and crumbling). Another problem with sutures is that since they need to be tied off to themselves or other sutures, they form a circular configuration around certain tissues and may strangulate the tissues within that circle. This strangulation causes reduced blood flow and potentially damaging ischemia for those tissues. In addition, the suture does not distribute its force adequately to compress tissues outside of a very narrow plane described by the circle of the suture path. Another key problem with the current treatment is the time taken to achieve suture hemostasis. Massive bleeding must be stopped quickly or the patient will exsanguinate (bleed a lot) and die. Placement of sutures is a time consuming process given the tools available today, the friable nature of parenchymal tissue, and the undesirability of intra-hepatic gauze packing.

The size and curvature of currently marketed needles is pre-set by the manufacturer. Current needles are not long or big enough to transfix major liver lacerations. Even if the needle was large, the suture method of repair causes inadequate force distribution to create hemostasis and resist progressive wound tearing.

New devices, procedures and methods are needed to support the strategy of damage control in patients who have experienced massive visceral injury. Such devices and procedures are particularly important in the emergency, military, and trauma care setting. These new devices, specifically parenchymal bolts, rely on the principles of broad force distribution on the tissue, pressure tamponade, ease of placement, ease of locking in place with the pressure pads, the ability to adjust tension to optimize tissue compression, and the lack of progressive tearing of the friable wound due to the high shear caused by the suture.

SUMMARY OF THE INVENTION

The devices and methods described below provide for improved haemostatic tissue apposition, especially in trauma care. The basic device is a transfixing trans-parenchymal bolt and a pressure plate with a securing bore adapted receive and securely grip the bolt. Key features of the bolt include column strength, adjustable depth of penetration, flexibility, tissue non-reactivity, quick and simple application, and adjustment of the pressure plates. The trans-parenchymal bolt uses pressure plates that are affixed to the ends of the bolt to distribute the pressure over a wide area of tissue and compress the tissue. The key features of the pressure plates include one-way ratcheting with quick release or a friction lock, ability to quickly and cleanly remove the pressure plate, and the ability to adjust the pressure plate to ensure optimum tissue apposition and compression. The trans-parenchymal bolt and pressure plate system generates pressure tamponade to provide for wound hemostasis. The trans-parenchymal bolt may be placed through an open surgical access site or through a laparoscopic access and manipulation system.

Once the bolt has been placed, it remains in place either temporarily or permanently. Temporary placement necessitates removal of the bolt. The bolt may be made from materials that permit long-term implantation or it may be fabricated from resorbable materials that obviate the need to remove the bolt in a subsequent surgical procedure. Both the bolt and the pressure plates are fabricated from materials with smooth outer surfaces that do not encourage tissue or clot ingrowth. The bolts and pressure plates are radiopaque and can be visualized on fluoroscopy or X-ray. Thus, the bolts and pressure plates may be removed with minimal re-bleeding.

The current medical practice of utilizing sutures is not an optimized solution to open visceral wound repair. Sutures were not designed for use in parenchymal tissue. The present invention distinguishes over the current medical practice because the present invention is tailored to the needs of open visceral wound repair. The parenchymal bolts are stiff enough to serve as their own needles, trocars, or stylets. They may be flexed or permanently deformed to achieve the desired tissue compression. They are suited for either open surgical implantation and removal, or they are suited for laparoscopic placement and removal using specialized access, grasping and delivery instruments. When the trans-parenchymal bolts of the present invention are removed from the patient, re-bleeding does not occur because there is minimal penetration of the wound tissues or clot into the interstices of the bolt and pressure plate.

DETAILED DESCRIPTION OF THE INVENTION

Figure 1A:
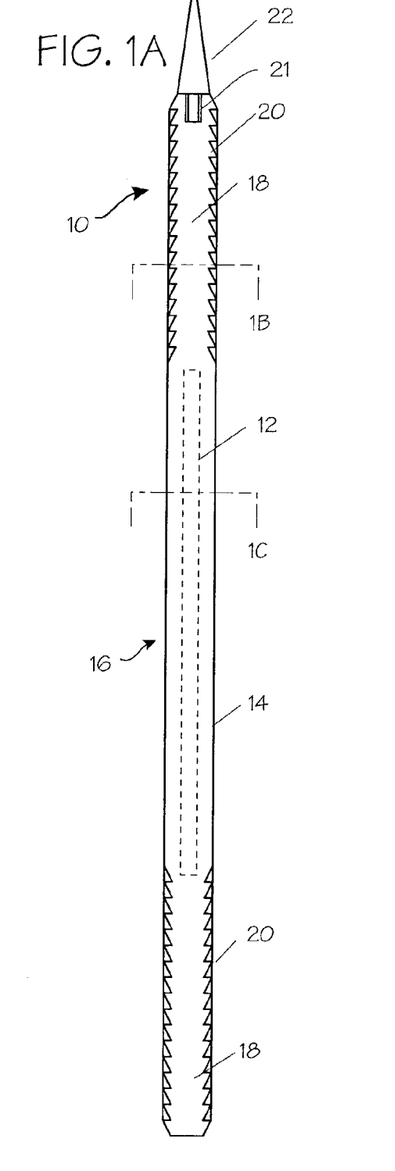
FIG. 1A illustrates a longitudinal cross-sectional view of the parenchymal bolt.

FIG. 1A illustrates a longitudinal cross-sectional view of a parenchymal bolt 10 of the present invention. The parenchymal bolt 10 comprises an inner core 12, an outer coating 14, a central region 16, two ends 18, and a plurality of serrations 20 on one or both ends 18. The parenchymal bolt 10 further comprises an optional pointed tip or trocar 22. The inner core 12 of the parenchymal bolt 10 is coaxially affixed to interior of the outer coating 14. The central connecting region 16 is disposed between the ends 18. One or both of the ends 18 of the parenchymal bolt 10 comprise a plurality of serrations 20 disposed longitudinally, along at least one side of one or more ends 18. The optional pointed tip or trocar 22 is removably affixed coaxially to one or more of the ends 18. The inner core 12 of the parenchymal bolt 10 provides column strength and the ability to be malleable or elastomeric, depending on the patient requirements. The preferred configuration of the inner core 12 is that it is malleable and located in the central region 16 only. The ends 18 are, preferably, elastomeric and do not have the malleable inner core 12 disposed therethrough. An advantage of having only polymeric material comprise the ends 18 is that the ends can be easily cut off or trimmed to size once the parenchymal bolt 10 is fully installed or placed in the patient (though the inner core may extend completely from end-to-end should the additional strength of this construction be needed, and trimming can be accomplished readily during an operation). Column strength is important so that tension may be transmitted through the parenchymal bolt 10, even when the parenchymal bolt 10 has been bent into an arc. Column strength also permits the parenchymal bolt 10 to be forced through tissue much the same as a suture needle would be forced through tissue. Malleability is important so that the parenchymal bolt 10 can be bent into the correct curvature needed for optimum coaptation of the tissue being repaired.

The inner core 12 is fabricated from materials such as stainless steel, cobalt-nickel alloys, nitinol, tantalum, titanium, polylactic acid, polyglycolic acid, platinum, and the like. The inner core 12 is preferably radiopaque and visible under fluoroscopy or X-Ray. It is important that the parenchymal bolt 10 be radiopaque so that the position of bolts can be confirmed after implantation, though radiolucent materials may also be used when appropriate. The outer coating 14 may be fabricated from polymers such as, but not limited to, polypropylene, polyethylene, polyester, polyurethane, polylactic acid, polyglycolic acid, polyimide or copolymers of these materials. In a preferred embodiment, the bolt 10 comprises radiopaque markers. The markers are fabricated from tantalum, gold, platinum, stainless steel, titanium, nitinol, cobalt nickel alloys and the like. The markers show the extents of the outer coating 14. The addition of barium, barium compounds, or the like in concentrations of up to about 40% in the polymer provides for radiopacity. The outer coating 14 may also be made from the same materials as are used to fabricate the inner core 12. The outer coating 14 may be the same physical structure as the inner core 12 (that is, formed integrally with the core). Preferably, the outer coating 14 is smooth and does not allow tissue ingrowth.

One or both of the ends 18 comprise an optional sharpened or tapered tip 22 to pierce tissue with minimal resistance. The optional pointed tip or trocar 22 facilitates passage of the parenchymal bolt 10 through tissue. The pointed tip or trocar 22 may be removed to minimize further tissue damage while the parenchymal bolt 10 is in place, and for this purpose, a releasable attachment means is provided on the proximal end of the trocar 22. In a preferred embodiment, the pointed tip or trocar 22 is removably attached to the ends 18 by a male threaded stub 21 that is mated into a female threaded adapter on the end 18. A bayonet mount or friction fit is another suitable method of releasably attaching the pointed tip or trocar 22 to the end 18. In another embodiment, the pointed tip or trocar 22 may also be longitudinally disposed through the entire core of the parenchymal bolt 10 and is removed by simply withdrawing the trocar 22 from the parenchymal bolt 10. The removable sharp tip 22, in a further embodiment, is retractable within the end 18 of the parenchymal bolt 10.

One or more of the ends 18 comprise the plurality of serrations 20 that permit locking with devices that are attached to the parenchymal bolt 10 in a later process. The serrations 20 are, preferably, triangular in shape and project outward from the longitudinal axis of ends 18. One side of the triangular projection is perpendicular to the longitudinal axis of the end 18. The perpendicular side of the triangle may also be undercut. Another side is tapered away from the end 18 and forms a ramp moving inward from the end 18 toward the center 16 of the parenchymal bolt 10.

Figure 1B:
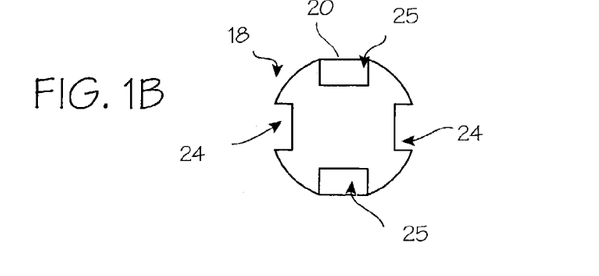
FIG. 1B illustrates a lateral cross-sectional view of the parenchymal bolt near one of the ends.

FIG. 1B illustrates a cross-section of the parenchymal bolt 10 taken near one of the ends 18. The cross-sectional view of the end 18 further comprises one or more optional tracking grooves 24 and one or more optional longitudinal ratchet slots 25. The tracking groove 24 is a slot and is disposed longitudinally along the length of ends 18. The longitudinal ratchet slot 25 is disposed longitudinally along the length of ends 18.

Referring again to FIGS. 1A and 1B, the serrations or ratchet teeth 20 are disposed within the ratchet slot 25. The height of the serrations is preferably smaller than the dept of the ratchet slot, so that the ratchet slot 25 holds and hides the serrations from the tissue as the parenchymal bolt 10 is advanced through the tissue to minimize trauma. The tracking groove 24 is used to provide alignment for parts that will be mated to the parenchymal bolt 10. By having two sets of tracking grooves 24, bilateral symmetry is achieved and parts can be mated in two orientations, rather than just one, thus facilitating the mating process. One ratchet slot 25 is required for each set of serrations and two ratchet slots 25 permit orientation of mating parts in more than one orientation. When more than one ratchet slot 25 and tracking groove 24 are used on each end, the second slot 25 or groove 24 is disposed 180 degrees around the end 18 circumference from the first slot 25 or groove 24.

Figure 1C:
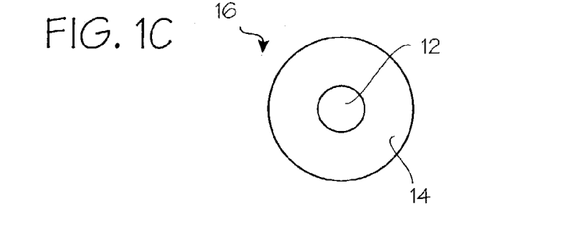
FIG. 1C illustrates a lateral cross-sectional view of the parenchymal bolt near the center.

FIG. 1C illustrates a cross-section of the central region 16 of the parenchymal bolt 10. The central region 16 comprises the core 12 and the outer coating 14. The outer coating 14 is disposed coaxially around the core 12. The optional tracking grooves 25 are not shown in this cross-section.

Figure 2A:
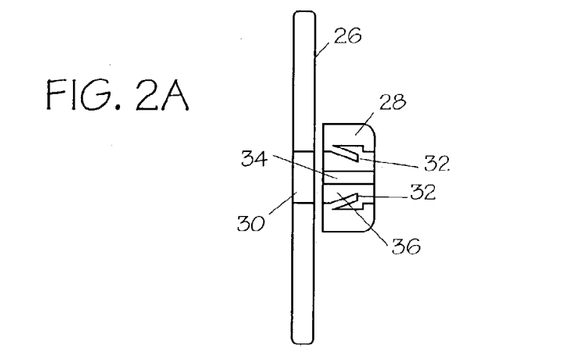
FIG. 2A illustrates a side view, of the pressure plate and locking nut in cross-section.

FIG. 2A illustrates a cross-sectional view of a pressure plate 26 and a ratcheting lock 28. The pressure plate 26 further comprises one or more pass through holes 30. The ratcheting lock 28 further comprises a plurality of locking tabs or pawls 32, a tracking protrusion or rail 34, and a central hole 36. The tracking rail 34 is sized and dimensioned to fit into the tracking groove 24 of the bolt end 18. The ratcheting lock 28 is disposed coaxially with the pass through hole 30 on the pressure plate 26. The ratcheting lock 28 may be affixed to the pressure plate 26, formed integral integrally with the pressure plate 26, or provided as a separate piece outside the pass through hole 30 of the pressure plate 26. The locking tabs 32 are flexibly affixed to the ratcheting lock 28 and project inward with a vertical edge toward the pressure plate 26 and a ramped edge sloping away from the pressure plate 26. The tracking protrusion 34 is one or more small projections into the central hole 36 of the ratcheting lock 28. The pressure plate 26 may have a single pass through hole 30 or it may have the plurality of pass through holes. With the plurality of pass through holes 30, one pressure plate 26 can be used with multiple parenchymal bolts 10.

Referring to FIGS. 1A, 1B, and 2A, the end 18 is configured to mate with the ratcheting lock 28 and the pressure plate 26. When the ratcheting lock 28 is advanced over one of the ends 18, through the central hole 36, the flexible locking tab or pawl 32 on the ratcheting lock 28 is bent aside by the ramp formed on the outside of serrations or ratchet teeth 20 and allows advancement of the ratcheting lock 28 to continue. Pulling backward on the ratcheting lock 28 or pressure plate 26 causes the vertical edge of the locking tab 32 to dig into the perpendicular sides described by the inner edges of the serrations 20 on the ends 18 so the ratcheting lock 28 will not slip backwards. The tracking protrusion 34 slidably mates with the alignment groove 24 on the end 18 to prevent the locking tabs 32 from becoming misaligned with the serrations 20 and inadvertently disengaging.

Figure 2B:
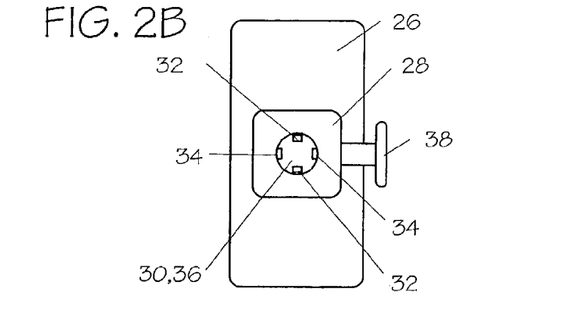
FIG. 2B illustrates an end view of the pressure plate and locking nut also showing the lock release.

FIG. 2B illustrates an end view of the pressure plate 26 and the ratcheting lock 28. As seen in this view, the ratcheting lock 28 further comprises a lock release 38. The locking tabs 32 project inward toward the center of the central hole 36 in the ratcheting lock 28. The lock release 38 is activated by manual pressure or by a laparoscopic instrument to bend back and release the locking tab 32 from the serrations 20 so that the ratcheting lock 28 and pressure plate 26 may be removed from the end 18. The lock release 38 allows for quick release of the ratcheting lock 28 and pressure plate 26. In another embodiment, the lock release 38 retracts the tracking protrusions 34 so that the ratcheting lock 28 can be rotated to disengage the locking tabs 32 from the serrations 20 and enable removal of the ratcheting lock 28 and the pressure plate 26 from the parenchymal bolt 10.

The pressure plate 26, the ratcheting lock 28 and the lock release 38 are fabricated from the same materials as are used in fabrication of the parenchymal bolt 10. All parts are designed with smooth outer surfaces to minimize the opportunity for tissue or thrombus ingrowth. The pressure plate 26 is stiff enough to distribute pressure to gently hold the tissue together while it heals. In a preferred embodiment, the pressure plate 26 and the ratcheting lock 28 are radiopaque. Materials such as barium, barium compounds, or radiopaque metals or the like, comprise at least part of the pressure plate 26 or lock 28. The pressure plate 26 and the lock 28 comprise, at least in part, the materials including those used in fabrication of the core 12 and the outer coating 14.

The length of the parenchymal bolt 10 ranges from 0.5 cm to 500 cm depending on the tissue being compressed. More preferably, the length of the parenchymal bolt 10 ranges from 2 cm to 50 cm (about 1 to 20 inches). The diameter of the parenchymal bolt 10 varies and is in proportion to the length of the bolt 10. Diameter ranges of between 0.5 mm and 10 mm are appropriate for the parenchymal bolt 10. The pressure plate 26 is sized to the organ being compressed. The pressure plate 26 has roughly rectangular dimensions ranging from a minimum of 0.5 cm to a maximum of 100 cm. The preferred range of sizes for the pressure plate 26 is 1 cm to 20 cm (about 0.5 inches to 8 inches). The pressure plate 26 thickness ranges from 0.5 mm to 30 mm.

Figure 3:
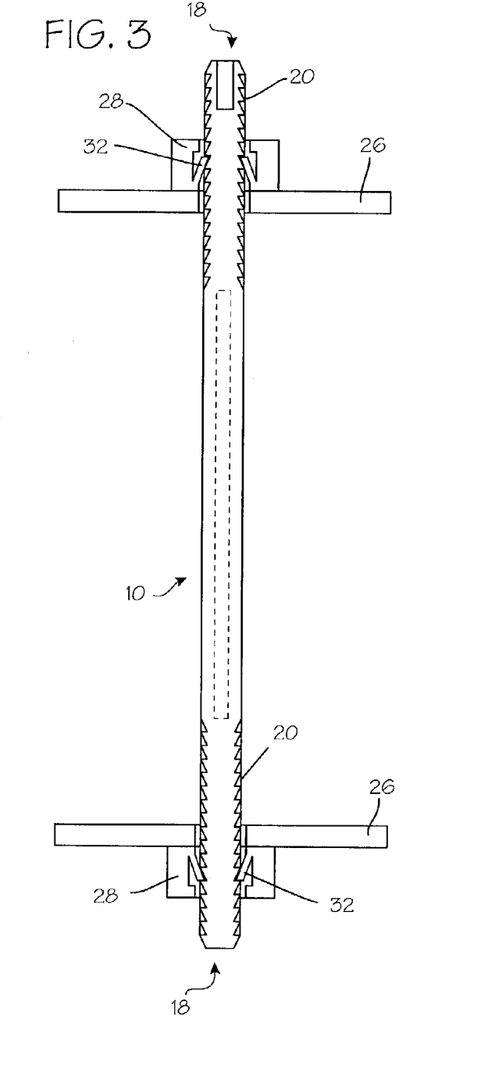
FIG. 3 illustrates a longitudinal cross-sectional view of the parenchymal bolt, two pressure plates and two locking nuts.

FIG. 3 illustrates a longitudinal cross-sectional view of the parenchymal bolt 10 with two pressure plates 26 and two ratcheting locks 28. The pointed tip or trocar 22 has been removed in this view. The pressure plates 26 and ratcheting locks 28 have been pushed over the ends 18 of the parenchymal bolt so that the locking tabs 32 have engaged the serrations 20.

Figure 4:
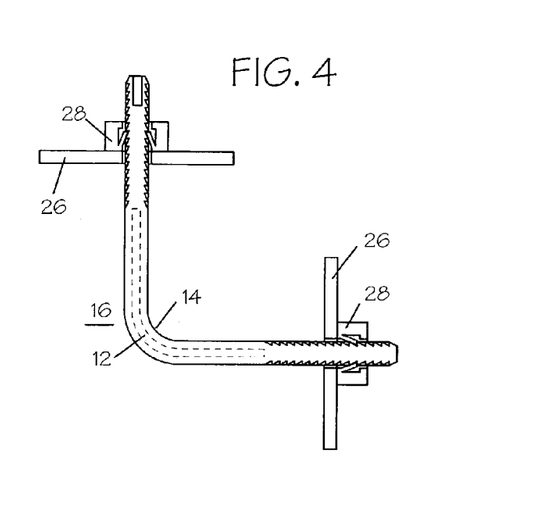
FIG. 4 illustrates a longitudinal cross-sectional view of the parenchymal bolt, two pressure plates and two locking nuts wherein the parenchymal bolt has been malleably deformed into a right angle bend.

FIG. 4 illustrates a longitudinal cross-sectional view of the parenchymal bolt 10 with two pressure plates 26 and two ratcheting locks 28. The parenchymal bolt 10 has been malleably deformed in its central region 16 and maintains that shape because the core 12 has sufficient strength to overcome the elastic forces generated by the outer covering 14.

Figure 5A:
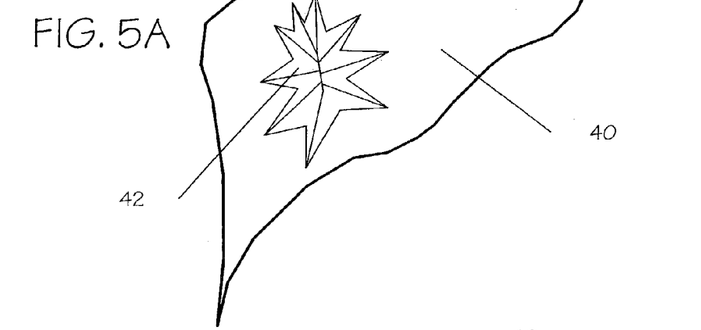
FIG. 5A illustrates a typical wound to the liver.
Figure 5B:
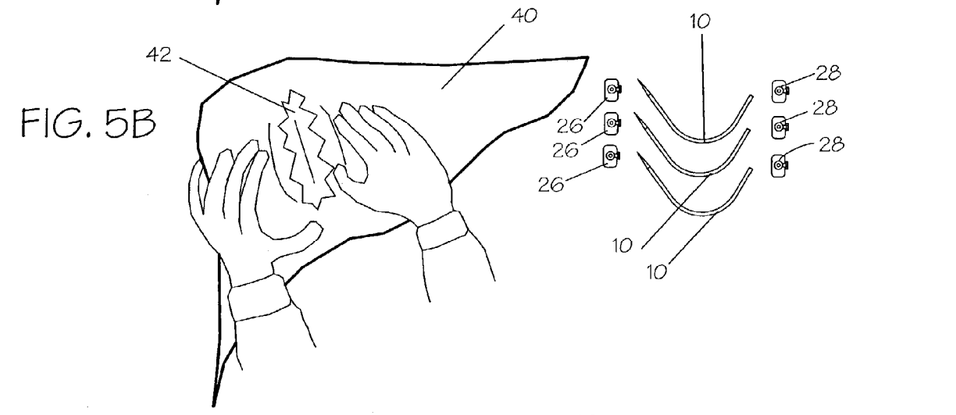
FIG. 5B illustrates preparations for open access liver wound hemostasis using three parenchymal bolts, six pressure plates and six ratcheting locks.
Figure 5C:
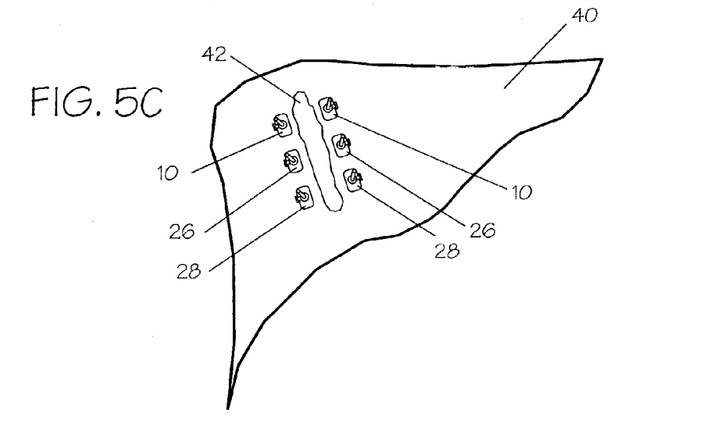
FIG. 5C illustrates the wound to the liver following temporary repair with three parenchymal bolts, six pressure plates, and six ratcheting locks.

FIGS. 5A through 5C illustrate the intended use of the parenchymal bolt. FIG. 5A illustrates a wound 42 in a liver tissue 40. The liver is a prime example of parenchymal tissue that often receives damage during abdominal trauma and during the surgery intended to repair that trauma. Note that the parenchymal tissue of the liver 40 is friable and unable to sustain high stresses without fracturing or tearing.

FIG. 5B illustrates open surgical preparation for repair of the liver wound 42 according to the methods of the present invention. The surgeon presses opposing sides of the rupture together, "approximating" the tissue on either side of the wound. Several parenchymal bolts 10, six pressure plates 26 and six ratcheting locks 28 are provided for the procedure while the liver 40 apposition is accomplished with manual pressure.

FIG. 5C illustrates completion of the repair of the wound 42 to the liver 40 using the parenchymal bolts 10, pressure plates 26 and ratcheting locks 28. After the bolts are bent into shape desired the by surgeon (any angle desired by the surgeon can be achieved manually), the surgeon shoves the bolts through the liver. The surgeon forces the bolts first into the liver on one side of the wound, and then upwardly and out of the liver on the other side of the wound, so that both ends of the bolt stick out of the liver with the ratchets exposed. The surgeon then slips the pressure plate and ratcheting locks onto each end. The ratcheting locks 28 are pushed onto the bolt, and tightened sufficiently to hold the pressure plates 26 firmly against the tissue causing complete wound 42 closure and hemostasis.

Figure 6A:
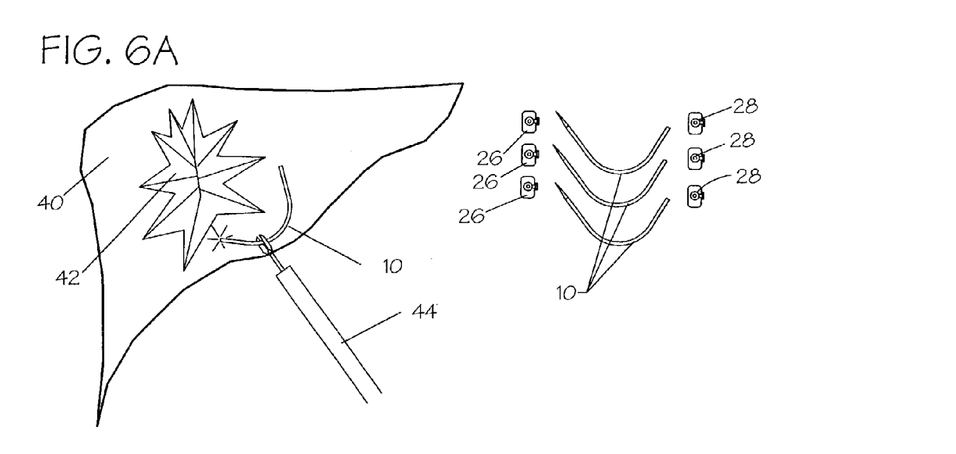
FIG. 6A illustrates a wound to the liver being repaired through laparoscopic access by application of a parenchymal bolt.
Figures 6B, 6C:
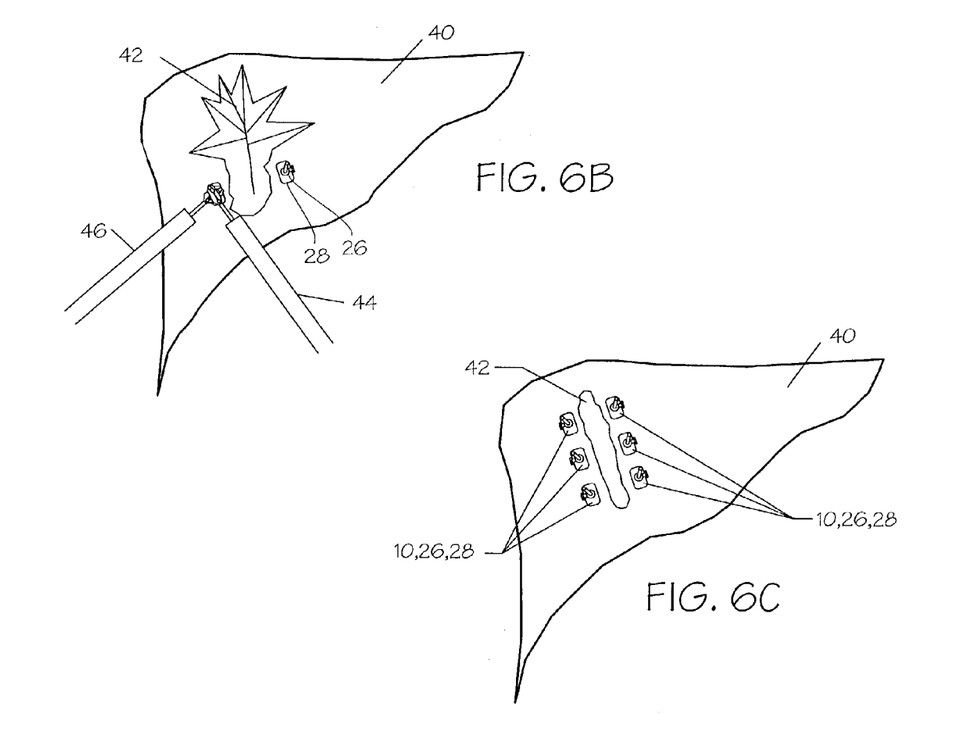
FIG. 6B illustrates application and tightening of a pressure plate and ratcheting lock via laparoscopic instrumentation.
FIG. 6C illustrates the wound to the liver following laparoscopic placement of three parenchymal bolts, six pressure plates, and six ratcheting locks.

FIGS. 6A through 6C illustrate a laparoscopic approach to approximating and securing the tissue of a ruptured organ using the bolts, pressure plates and ratchet mechanisms. FIG. 6A illustrates the wound 42 to the liver 40 with the parenchymal bolt 10 being applied by a laparoscopic instrument 44. In this embodiment, the laparoscopic instrument 44 is a grasper or set of jaws, placed through an axially elongate hollow structure, that may be manipulated by the surgeon from the outside of the patient. After the bolts are bent into shape desired the by surgeon (any angle desired by the surgeon can be achieved manually), the surgeon shoves the bolts through the liver. The bolts may be bent to shape before or after placement in to the laparoscopic workspace. Using the laparoscopic graspers, the surgeon forces the bolts first into the liver on one side of the wound, and then upwardly and out of the liver on the other side of the wound, so that both ends of the bolt stick out of the liver with the ratchets exposed.

FIG. 6B illustrates the wound 42 to the liver 40 following placement of the first parenchymal bolt 10, two pressure plates 26 and two ratcheting locks 28 using the first laparoscopic instrument 44 and a second laparoscopic instrument 46. Again, the laparoscopic instruments 44 and 46 are placed through an axially elongate hollow structure that provides access to the internal organs of the patient. The laparoscopic grasping device 46 is placed around the ratcheting lock 28 and is used to advance the ratcheting lock 28 and pressure plate 26 inward against the liver tissue 40. The laparoscopic grasping device 44 applies tension to the parenchymal bolt 10 so that the pressure plate 26 and the ratcheting lock 28 move relative to the parenchymal bolt 10. The laparoscopic grasping instruments 44 and 46, which may be similar to very long nosed pliers, may be replaced by a single instrument that performs both functions of stabilizing the parenchymal bolt 10 and advancing the ratcheting lock 28. This type of procedure is generally performed under direct vision through laparoscope placed within the surgical field, but may also be visualized with a video display fed by a camera attached to the endoscope.

FIG. 6C illustrates the wound 42 to the liver 40 following laparoscopic repair with three parenchymal bolts 10, six pressure plates 26 and six ratcheting locks 28. Thus, FIGS. 5A through 5C and 6A through 6C illustrate the manufacture of a tissue approximating device by bending a malleable bolt, forcing the bolts through the body tissue, and fitting a pressure distributing plate onto the ends of the bolt and forcing the pressure plates into contact with the body organ, and securing the pressure plates in fixed longitudinal relationship with the bolt by fixing the ratcheting lock onto the ends of the bolts, and forcing the pressure plate and ratcheting locks into contact with the body tissue. The ratchet structure of the bolt and the ratchet lock comprise a means for longitudinally fixing the pressure plate along the length of the bolt. Other means for fixing the pressure plate, including threaded nuts combined with outside threads on the bolt ends, may be also be used to accomplish this function. For body tissue such as internal organs, which present a single surface in the operating field, the bolts are bent and forced through the organ such that both ends protrude from the presenting surface of the organ.

Figure 7A:
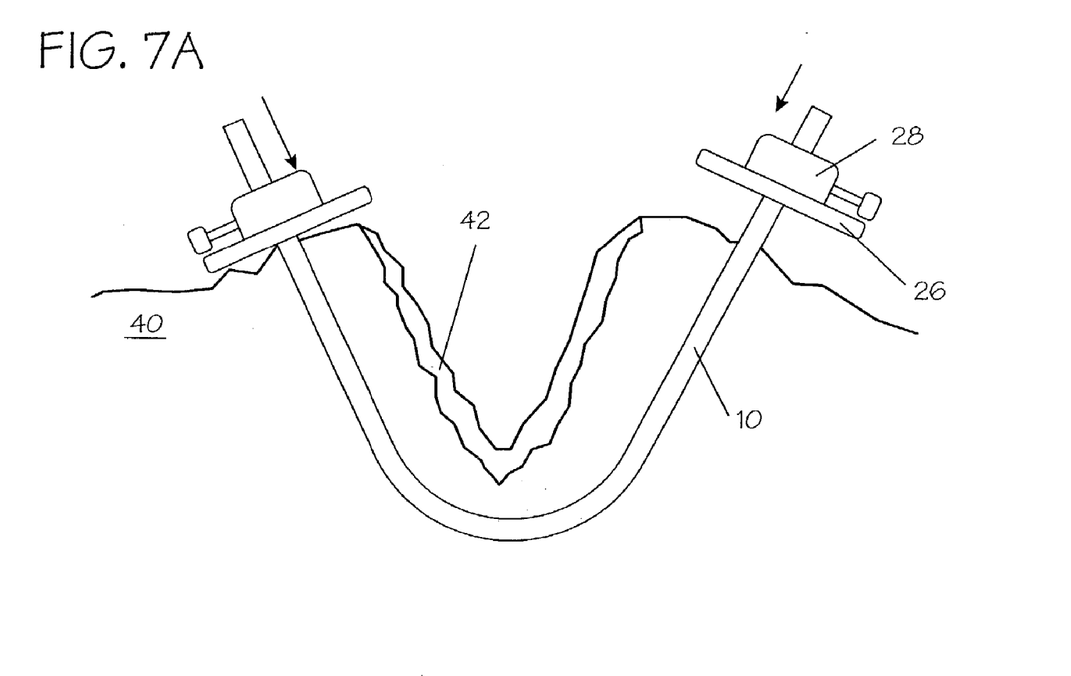
FIG. 7A illustrates a side cross-sectional view of a parenchymal tissue injury with a parenchymal bolt, two pressure plates, and two ratcheting locks prior to tightening.

FIG. 7A illustrates a side cross-sectional view of the wound 42 to parenchymal tissue 40, in this case the liver 40, following initial repair with the parenchymal bolt 10 of the present invention. The repair of the wound 42 comprises placement of the parenchymal bolt 10 followed by placement of two pressure plates 26 and two ratcheting locks 28.

Referring to FIG. 7A, FIG. 1A and FIG. 2A, the pointed tip or trocar 22 has been removed or retracted following full tissue 40 penetration by the parenchymal bolt 10. Two pressure plates 26 have been applied to the ends 18 of the parenchymal bolt 10 to transfix the tissue 40. Two ratcheting locks 28 are in the process of being tightened over the pressure plates 26 and the wound 42 is still open.

Figure 7B:
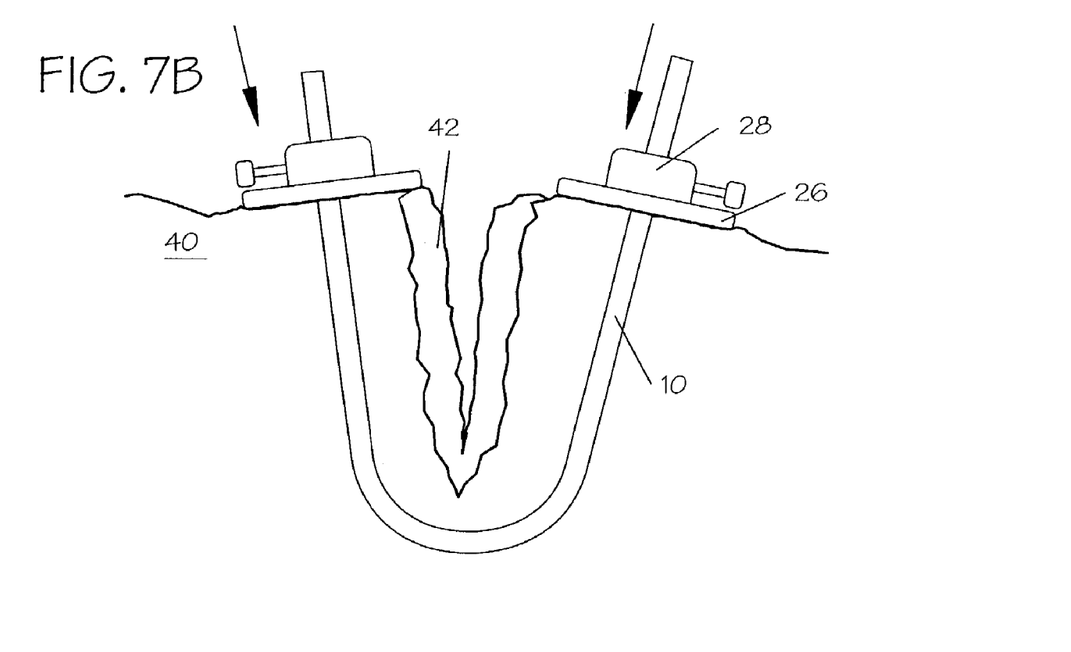
FIG. 7B illustrates a side cross-sectional view of the parenchymal tissue injury during tightening of the ratcheting locks.

FIG. 7B illustrates the wound 42 in the parenchymal tissue 40 at a point where the ratcheting locks are nearly tightened against the tissue 40. The wound 42 has achieved nearly complete closure. Additional inward tightening of the ratcheting locks 28 will compress the pressure plates 26 and achieve full wound 42 closure and hemostasis. The surgeon may bend the bolts after placement, as seen in FIG. 7B, to help pull the edges of the wound together. The parenchymal bolt 10 flexes to accommodate the change in wound geometry as the ratcheting locks 28 are tightened.

Figure 8:
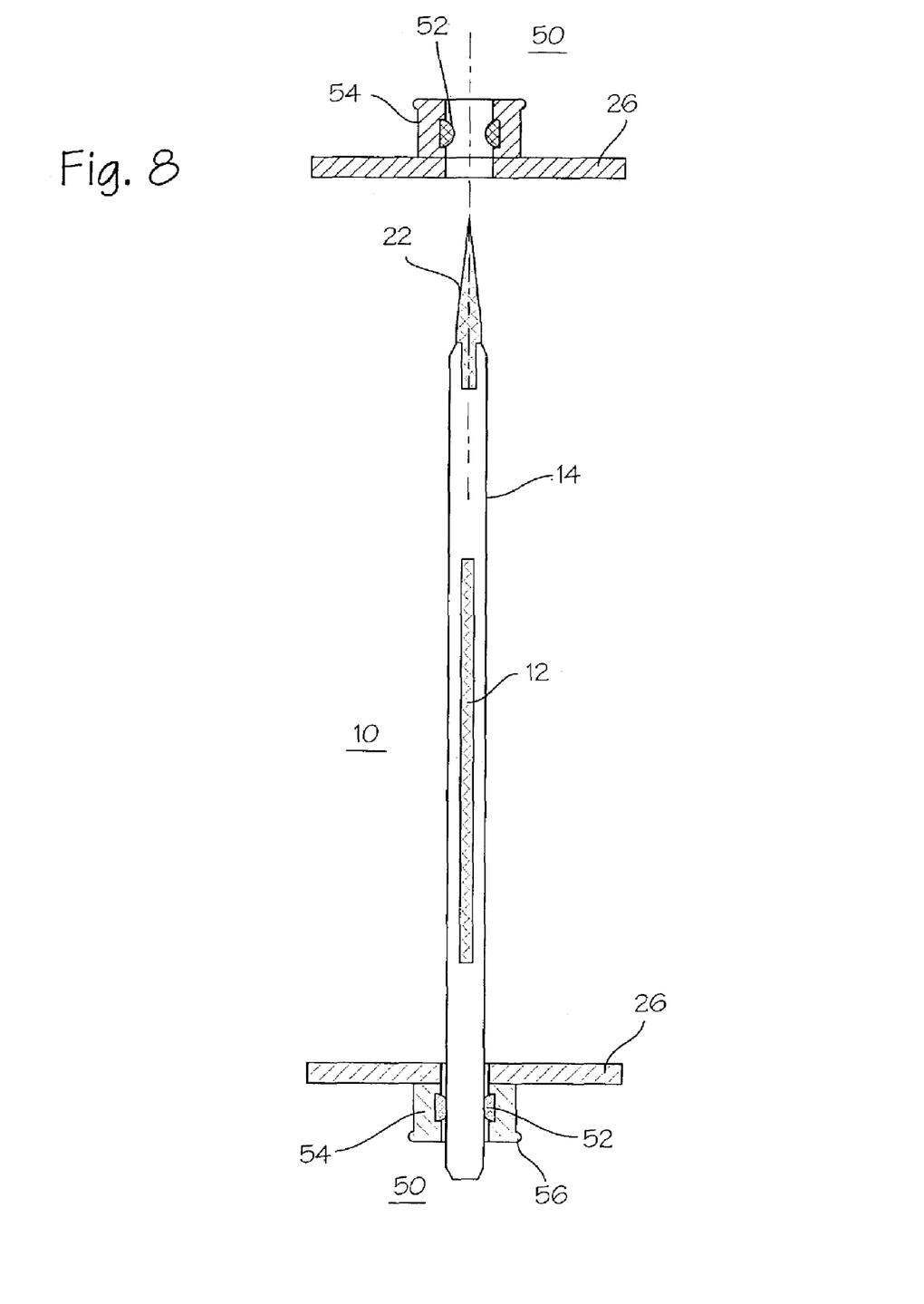
FIG. 8 illustrates a longitudinal cross-sectional view of a parenchymal bolt comprising pressure plates and friction locks.

FIG. 8 illustrates another embodiment of the parenchymal bolt 10, shown in longitudinal cross-section. The parenchymal bolt 10 further comprises an axially elongate shaft 14, a malleable central component 12, a sharpened tip 22, one or more pressure plates 26, and one or more friction locks 50. The friction lock 50 further comprises a friction generator 52 and a housing 54, which further comprises a grasping bump 56. The friction lock 50 may be separate or integral to the pressure plate 26. The friction lock 50 is fabricated from biocompatible polymeric materials such as, but not limited to polyethylene, polypropylene, ABS, PVC, stainless steel, PTFE, titanium, PLA, PGA, and the like. In the preferred embodiment, the friction lock 50 comprises a friction generator 52, which is a disc with a hole in the center. The hole is smaller in diameter than the outside diameter of the axially elongate shaft 14 of the parenchymal bolt 10. The friction generator 52 comprises elastomeric materials that exert an inward pressure and generate friction against the outside diameter of the axially elongate shaft 14. Such elastomeric materials include, but are not limited to, polyurethane, silicone elastomer, latex rubber, and the like. The friction exerted by the friction lock 50 against the axially elongate shaft 14 is sufficient to resist the force of the tissue resilience once engaged in contact but insufficient to prevent manual movement generated by the surgeon either applying or removing the friction lock 50 from the axially elongate shaft 14. The housing 54 further comprises a grasping surface 56, which is a bump or other feature that allows for easy grasping by the surgeon in a wet or slick environment so that the friction lock 50 may be removed retrograde from the shaft 14 of the parenchymal bolt 10. Other embodiments of the friction lock 50 include those that comprise a jam cleat, an over-center cam, a spring-loaded friction member, and the like. The friction lock 50 preferably does not comprise a release mechanism but in certain configurations, a button or latch to release the friction is required.

Application of the parenchymal bolt system provides improved speed of solid organ trauma repair and minimizes the chance of tissue tearing or fracture, relative to the use of sutures for said repair. The parenchymal bolt system provides pressure tamponade to the injured tissue to provide for hemostasis and maximize the recovery process while minimizing complications common to suture-based approaches.

The present invention may be embodied in other specific forms without departing from its spirit or essential characteristics. For example, the ratcheting locks could be replaced by simple threaded nuts that engage threads on the parenchymal bolt. The bolt may comprise telescoping tubes that slide and lock relative to each other, thus obviating the need to cut off excess material projecting away from the pressure plate. Additionally, though described in the context of internal organs, the device and methods may be used to approximate wounds in muscle tissue or fibrous tissue. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A method of achieving wound hemostasis and closure for soft body tissue, comprising the steps of:
   applying a bolt, wherein the bolt comprises a single axially elongate shaft having a distal, pointed end and a proximal end, through tissue surrounding a wound, wherein the distal end and the proximal end of the bolt are exposed outside the tissue;
   applying a first pressure plates to the distal, pointed end of said shaft, wherein the distal, pointed end extends beyond the first pressure plate;
   applying a second pressure plate to the proximal end of said shaft, wherein the second end extends beyond the second pressure plate;
   applying a first lock to the distal, pointed end of the shaft;
   applying a second lock to the proximal end of the shaft, wherein said second lock comprises an adjustment mechanism; and
   adjusting the position of the second pressure plate and lock with the adjustment mechanism on the proximal end of the bolt to maintain said first and second pressure plates in compression against said tissue as constrained by said bolt to achieve wound closure and hemostasis.

2. The method of claim 1 further comprising the step of removing or retracting the distal, pointed end of the bolt.

3. The method of claim 1 wherein the placement of said bolt is accomplished through an axially elongate hollow introduction device.

4. The method of claim 3 further comprising the step of directly visualizing the placement of the bolt.

5. The method of claim 1 wherein removal of said bolt is accomplished through an axially elongate hollow introduction device.

6. The method of claim 1 further comprising the step of removing the bolt at from the tissue.

7. The method of claim 1 further comprising the step of implanting the bolt in body tissue for a long period of time.

8. The method of claim 1 further comprising the step of allowing the bolt to resorb.

9. The method of claim 1 further comprising the step of bending the bolt into an arcuate shape prior to applying the bolt through the tissue.

10. The method of claim 1 further comprising the step of visualizing the bolt using fluoroscopy or X-rays.

11. A method of manufacturing a medical device for approximating wounded soft body tissue comprising:
    providing a malleable bolt comprising a single, axially elongate shaft and having first and second ends, wherein the first end of the bolt comprises a tapered point;
    providing first and second pressure plates adapted to slide over each of the first and second ends of the bolt;
    providing first and second locking mechanisms adapted to longitudinally fix the first and second pressure plates, respectively, along the length of the bolt;
    forcing the first end of the bolt through body tissue until the first and second ends of the bolt extend from the tissue;
    affixing the first pressure plate on the first end of the bolt;
    placing the second pressure plate on the second end of the bolt;
    affixing the first locking mechanism on the first end of the bolt, to maintain the position of the first pressure plate;
    placing the second locking mechanism on the second end of the bolt;
    forcing the first and second pressure plates into contact with the body tissue; and
    adjusting the position of the second pressure plate and second lock, relative to the second end of the axially elongate shaft, to achieve a desired amount of tissue compression.

12. The method of claim 11 further comprising the steps of bending the malleable bolt, and forcing the bolt through body tissue so that both ends of the bolt protrude from an accessible surface of the body tissue.

13. The method of claim 11 further comprising the step of removing the bolt.

14. The method of claim 11 wherein the first lock and the first pressure plate are integral to each other and the second lock and the second pressure plate are integral to each other.

15. The method of claim 11 further comprising the step of advancing the tapered point to pierce the tissue as the bolt is being forced through the body tissue and retracting the tapered point once the forcing step is completed.

16. the method of claim 11 further comprising the steps of applying a plurality of bolts to the body tissue.

17. the method of claim 11 comprising the step of forcing the bolt through solid organ tissue.

18. The method of claim 11 comprising the step of forcing the bolt through muscle tissue.

19. A method of achieving wound closure for soft body tissue, comprising the steps of:
    applying a bolt, comprising a single, axially elongate shaft with a first, sharpened end and a second, blunt end, through a region of tissue surrounding a wound so that the first, sharpened end and the second, blunt end of the bolt are exposed outside the tissue;

applying a pressure plate and a lock at each end of the shaft;

adjusting the position of the pressure plate on the second blunt end of the bolt, relative to the axially elongate shaft, to achieve a desired amount of wound closure; and activating the locks to keep said pressure plates in compression against said tissue as constrained by said bolt to achieve wound closure.

20. The method of claim 11 wherein the adjustment step comprises actuating a ratchet mechanism.

* * * * *